United States Patent

Ohno et al.

[11] Patent Number: 5,444,171
[45] Date of Patent: Aug. 22, 1995

[54] METHOD FOR PURIFICATION OF 1,1,1,2-TETRAFLUOROETHANE

[75] Inventors: Hiromoto Ohno; Toshio Ohi; Hidetoshi Nakayama; Kazuo Muramaki, all of Kawasaki, Japan

[73] Assignee: Showa Denko Kabushiki Kaisha, Tokyo, Japan

[21] Appl. No.: 961,869

[22] Filed: Oct. 15, 1992

[51] Int. Cl.6 .............................................. C07C 17/38
[52] U.S. Cl. .................................... 570/177; 570/166; 570/169
[58] Field of Search ........................ 570/177, 166, 169

[56] References Cited

U.S. PATENT DOCUMENTS 4,158,675  6/1979  Potter .

FOREIGN PATENT DOCUMENTS

| 0446869 | 9/1991 | European Pat. Off. . |
| 0449614 | 10/1991 | European Pat. Off. . |
| 0449617 | 10/1991 | European Pat. Off. . |
| 0592711 | 4/1994 | European Pat. Off. ............ 570/177 |
| 43-010601 | 5/1968 | Japan . |
| 56-038131 | 9/1981 | Japan . |
| 62-023728 | 5/1987 | Japan . |

Primary Examiner—Alan Siegel
Attorney, Agent, or Firm—Sughrue, Mion, Zinn, Macpeak & Seas

[57] ABSTRACT

In the production of 1,1,1,2-tetrafluoroethane by reacting trichloroethylene with hydrogen fluoride, crude 1,1,1,2-tetrafluoroethane is highly purified by a method comprising subjecting the crude 1,1,1,2-tetrafluoroethane to preliminary purification to remove hydrogen chloride to a concentration of not higher than 2%, and bring the preliminarily purified 1,1,1,2-tetrafluoroethane containing one or more unsaturated impurities and hydrogen fluoride in an amount at least equimolar to the unsaturated impurities into contact with a fluorination catalyst in a vapor phase to decrease the content of the unsaturated impurities.

6 Claims, No Drawings

METHOD FOR PURIFICATION OF 1,1,1,2-TETRAFLUOROETHANE

BACKGROUND OF THE INVENTION

1. Field of the Invention

This invention relates to the purification of 1,1,1,2-tetrafluoroethane by causing at least one unsaturated impurity contained in the 1,1,1,2-tetrafluoroethane to react with hydrogen fluoride (HF).

More particularly, this invention relates to a method for the purification of 1,1,1,2-tetrafluoroethane (hereinafter referred to briefly as "HFC-134" or "$CF_3CH_2F$"), which has been attracting attention as a prospective substitute for CFC-12, which is a refrigerant used extensively in automobile air conditioners, refrigerators, etc. that is hazardous to the environment, particularly, the ozonosphere.

2. Description of the Prior Art $CF_3CH_2F$ is produced using a method that comprises fluorinating by using a chromium type catalyst 1,1,1-trifluoro-2-chloroethane (hereinafter referred to as "HCFC-133a" or "$CF_3CH_2Cl$") which is produced on a commercial scale as a raw material for trifluoroethanol [KOKOKU (Japanese Examined Patent Publication) No. 43-10601 and U.S. Pat. No. 4,158,675], a method that comprises adding hydrogen fluoride to trifluoroethylene ($CF_2=CHF$) (KOKOKU No. 62-23728), and a method that comprises causing 2,2-dichloro-1,1,1,2-tetrafluoroethane ($CF_3CCl_2F$) or 2-chloro-1,1,1,2-tetrafluoroethane ($CF_3CHClF$) to react with hydrogen in the presence of a palladium catalyst (KOKOKU No. 56-38131) have been known.

When these methods are adopted for the production of $CF_3CH_2F$, the relevant reactions entail by-productions of various impurities depending on the used catalyst, reaction conditions, etc.

The impurities occurring as by-products in the reactions include unsaturated impurities such as $CF_2=CClF$, $CClF=CHCl$, $CF_2=CHCl$, $CHF=CClF$, $CF_2=CHF$, and $CHCl=CHF$, chlorofluorocarbons such as $CCl_2F_2$, $CH_2ClF$, $CH_2Cl.CClF_2$, $CF_3CHCl_2$, and $CF_3CHClF$, and hydrofluorocarbons such as $CF_3CHF_2$, $CF_3CH_3$, and $CHF_2CHF_2$, for example.

Of these impurities, the produced $CF_3CH_2F$ tolerates the presence of hydrofluorocarbons when their contents are small but does not tolerate the presence of unsaturated impurities and chlorofluorocarbons even when their contents are extremely small. These impurities, therefore, are removed from the product by fractional distillation, for example.

The impurities that have boiling points close to the boiling point of $CF_3CH_2F$ and the impurities that occur in the form of an azeotrope, however, are extremely difficult to be removed by distillation. Particularly, the unsaturated impurities persist as trace impurities in the product even after distillation.

Various processes have been proposed so as to overcome the difficulties encountered in the distillation.

(1) In the conventional method for the production of HFC-134a, trichloroethylene as a raw material and HF are introduced into a first reactor. The produced gas is composed predominantly of HCFC-133a, hydrogen chloride (HCl), and unreacted HF.

When this produced gas is introduced as it is into a second reactor, and since it contains hydrogen chloride in a large amount, the reaction that ensues forms a disadvantageous equilibrium, as represented by the formula (1), and produces virtually no HFC-134a, the desired product.

$$CF_3CH2Cl + HF \sim CF_3CH_2F + HCl \tag{1}$$

This gas, therefore, is subjected to separation and removal of hydrogen chloride by using a purifying system.

The remaining gas, either as it is or after replenishment of HF, is introduced into the second reactor. The gas produced in the second reactor is a mixture consisting of unreacted HCFC-133a and HF, desired HFC-134a, by-products comprising mainly unsaturated impurities, and hydrogen chloride.

This gas is supplied as it is to a third reactor and subjected therein to a reaction for the addition of HF to the unsaturated impurities. The gas produced in the third reactor is forwarded to a purifying system for the purpose of separation and removal of hydrogen chloride. The remaining gas is forwarded to a separating and purifying system to effect isolation of HFC-134a as the product aimed at. The HCFC-133a and HF, which are expelled from the HFC-134a, are recycled to the second reactor.

This process entails a decline in the efficiency of the reaction of the unsaturated impurities because the outlet gas from the second reactor is introduced into the third reactor in a form still containing HCl. It also suffers from a disadvantage in that the reactor is required to have a larger capacity because the effluent gas contains the HCFC-133a and HF in a large amount relative to the desired HFC-134a. The solution of this problem necessitates interposition of a purifying system between the second reactor and the third reactor and consequently entails an addition to the cost of equipment.

(2) Other processes have been proposed by the inventions disclosed in EP-O 446 869-A1, EP-O 449 614-A2, and EP-O 449 617-A2, for example.

In accordance with these processes of production, HCFC-133a and HF are supplied to a second reactor and the product of the reaction therein is a mixture consisting of the unreacted starting materials of HCFC-133a and HF, desired product of HFC-134a, by-products of HCFC-1122 ($CF_2=CHCl$) and the like, and hydrogen chloride.

This mixed gas is supplied as it is to a first reactor. At the same time, trichloroethylene as the raw material and HF are supplied thereto. The trichloroethylene reacts with HF to produce HCFC-133a and hydrogen chloride and HCFC-1122 reacts with HF and consequently converts into HCFC-133a.

The produced gas that occurs in the first reactor, therefore, is a mixture that consists of HCFC-133a, HFC-134a, HF, hydrogen chloride, a small amount of trichloroethylene, and other by-products. This produced gas is forwarded to a purifying system for the separation and removal of hydrogen chloride and for the subsequent separation of HFC-134a. The remaining HCFC-133a and HF are returned to the second reactor.

Though this procedure is characterized by diluting the reaction gas prior to the reaction in consideration of large exothermicity of the trichloroethylene reaction with HF, it entails the following drawbacks.

(a) In the above method (2), since the hydrogen chloride-containing effluent gas from the second reactor is wholly introduced into the first reactor, the concentration of hydrogen chloride within the first reactor is increased and the efficiency of the reaction of the unsaturated impurities by the procedure is lowered compared with the conventional method of (1).

(b) Further, since the produced gas from the second reactor is wholly introduced into the first reactor, the amount of gas to be received in the first reactor is increased and the reaction system requires an increased capacity compared with that required by the conventional method.

SUMMARY OF THE INVENTION

This invention has as an object to provide a novel method for the purification of 1,1,1,2-tetrafluoroethane without entailing the drawbacks characteristic of the prior art as described above.

In light of the drawbacks of the prior art described above, the present inventors pursued a diligent study with a view to developing a commercially feasible and economical method for the purification of HFC-134a. They have consequently found that in the production of HFC-134a by the reaction of trichloroethylene with hydrogen fluoride, a significant amount of HFC-134a of high purity containing no unsaturated impurities can be produced economically and easily by causing HFC-134a containing at least one unsaturated impurity, having the hydrogen chloride content thereof lowered to below 2 mol %, and containing hydrogen fluoride in at least an equimolar ratio relative to the unsaturated impurity, preferably without further addition of hydrogen fluoride, to react with a catalyst in the vapor phase and recovering the HFC-134a from the reaction mixture. This invention has been completed by this finding.

Heretofore a method that comprises causing trichloroethylene to react with HF has been known in the art as a means of producing HFC-134a. This reaction cannot be accomplished in one step and is carried out by a two step procedure that uses different conditions. Specifically, the reaction of the first step represented by the formula (2), namely the reaction of trichloroethylene with HF for the formation of HCFC-133a:

$$CCl_2=CHCl+3HF \rightarrow CF_3CH_2Cl+2HCl \quad (2)$$

and the reaction of the second step represented by the formula (1) mentioned above, namely the reaction of HCFC-133a with HF for the formation of HFC-134a, are used.

The reaction of the second step, which comprises causing HCFC-133a to react with HF and consequently forming HFC-134a, is an equilibrium reaction and the reaction product contains an unsaturated impurity capable of forming an azeotrope with HFC-134a by the reaction. This unsaturated impurity is separated from HFC-134a only with difficulty, which has inspired the various processes mentioned above.

In a method formerly proposed by the present inventors for the production of HFC-134a (Japanese Patent Applications No. 4-19249 and No. 4-199827), a process is disclosed that comprises introducing the products of the reactions of the first and second steps jointly into a step for crude purification, effecting removal of a HCl by-product and the concentration of HFC-134a by using a simplified apparatus and consequently enjoying advantages such as a simplified distillation operation and lowered energy consumption.

The present invention provides a method for the purification of crude 1,1,1,2-tetrafluoroethane produced by reacting trichloroethylene with hydrogen fluoride comprising the steps of subjecting the crude 1,1,1,2-tetrafluoroethane to preliminary purification to remove hydrogen chloride to a concentration of not higher than 2%, and bringing the preliminarily purified 1,1,1,2-tetrafluoroethane containing one or more unsaturated impurities and hydrogen fluoride in an amount at least equimolar to the unsaturated impurities into contact with a fluorination catalyst in a vapor phase so as to decrease the content of the unsaturated impurities.

DETAILED DESCRIPTION OF THE PREFERRED EMBODIMENTS

This invention relates to economical, easy, and efficient purification of HFC-134a concentrated through the crude purification step by decreasing at least one unsaturated impurity contained in the HFC-134a. The method for effecting this purification is described below. The HFC-134a concentrated through the crude purification step by the process formerly proposed by the present inventors must have the hydrogen chloride content thereof repressed below 2 mol %. Preferably, it contains no hydrogen chloride.

If the hydrogen chloride content exceeds 2 mol %, the reaction for the addition of HF to the unsaturated impurity is inhibited. This reaction trend gains in conspicuity in proportion as the concentration of hydrogen chloride increases. As a result, the efficiency of the reaction is notably reduced even to the extent of necessitating an increase in the reaction temperature.

The heightened reaction temperature induces a reaction and decomposition of HFC-134a and HCFC-133a indicated in the formula (3) and the formula (4) so as to entail a reduction in the amount of HFC-134a. The product of the decomposition degrades the activity of the catalyst.

$$CF_3CH_2F+HCl \rightarrow CF_3CH_2Cl+HF \quad (3)$$

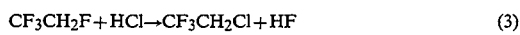

$$CF_3CH_2Cl \rightarrow CF_2=CHCl+HF \quad (4)$$

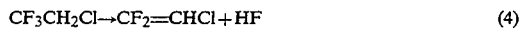

For this reason, the concentration of hydrogen chloride must be not more than 2 mol %. Preferably, this concentration is 0.

The method of this invention obviates the necessity for adding HF to the reaction gas because the HFC-134a that has undergone the crude purification step contains HF as an azeotropic component. The desired reaction proceeds with a high level of efficiency when HF and the unsaturated impurity are contained in at least an equimolar ratio. The unreacted HF is recovered after completion of the reaction and is put to use rather than discarded and wasted.

The concentration of HCFC-133a to be contained in HFC-134a is desired to be not more than 10 mol %. If the concentration exceeds 10 mol %, the operation is no longer economical because the efficiency of the reaction is degraded and the reaction system is required to be larger.

The concentration of HFC-134a is desired to be not less than 70 mol %. If the concentration is less than this limit, the operation is undesirable because it experiences the same drawbacks as in the case of HCFC-133a.

The HFC-134a that possesses the composition mentioned above and is in a concentrated state is compelled to react with a catalyst in the vapor phase.

The catalyst to be used in the method of this invention is only required to manifest a catalytic activity to the reaction of fluorination. Specifically, the catalysts that are usable effectively herein are fluorinating catalysts comprising compounds of metals of the Groups 1B, 2A, 2B, 4B, 5A, 5B, 6A, 7A, and 8 in the Long-Form Periodic Table of Elements and at least one element selected from the group consisting of Cu, Mg, Zn, Pb, V, Bi, Cr, Mn, Fe, Co, and Ni. This catalyst may be deposited on a support of alumina, aluminum fluoride, or activated carbon.

This catalyst can be produced by any of the conventional methods known in the art. For example, it can be produced by immersing alumina in an aqueous cobalt chloride solution, drying the impregnated alumina, and calcining the dried alumina under a current of air. The catalyst thus prepared should be activated with hydrogen fluoride before it is used in the reaction.

The reaction temperature should be in the range between 130° C. and 280° C., preferably between 150° C. and 250° C. The reaction of the unsaturated impurity proceeds at an unduly low speed if the reaction temperature is below the lower limit of the range mentioned above. The reaction and decomposition of HFC-134a and HCFC-133a mentioned above occurs, unfavorably, if the reaction temperature exceeds the upper limit.

After the reaction, the reaction product can be purified economically, easily, and efficiently to produce highly pure HFC-134a containing no unsaturated impurity because the unreacted HF is recovered and the small amounts of HCFC-133a and other fluorocarbons that are contained in the concentrated HFC-134a are effectively separated by distillation without forming any azeotrope among themselves because of the absence of HF.

In accordance with this invention, the heretofore extremely difficult removal of unsaturated impurities from $CF_3CH_2F$ can be accomplished efficiently, easily, and economically. This invention, therefore, allows the production of $CF_3CH_2F$ with a high level of purity.

This invention is described more specifically with reference to the following non-limitative examples.

CATALYST PREPARATION EXAMPLE 1

In a solution of 3.6 g of cobalt chloride ($CoCl_2$) in 52 ml of purified water, 100 ml of activated alumina (produced by Nikki Universal K.K. and marketed under product code of "NST-3") was kept immersed until the alumina absorbed the whole volume of the solution. Then, the alumina wetted with the solution was dried over a water bath at 90° C.

Within an air circulation type hot air drier, the catalyst was further dried at 110° C. for 10 hours. The dry catalyst was filled in a glass calcination tube and heated to 400° C. under air flowing at a space velocity (SVo) of 500 $hr^{-1}$, to obtain a catalyst.

CATALYST PREPARATION EXAMPLE 2

A catalyst was prepared by repeating the procedure of Catalyst Preparation Example 1, except that 6.67 g of nickel chloride ($NiCl_2.6H_2O$) was used instead of cobalt chloride ($CoCl_2$).

RAW MATERIAL EXAMPLE 1

The crude purification product obtained by causing trichloroethylene ($CCl_2=CHCl$) to react with hydrogen fluoride in the vapor phase in the presence of a chromium catalyst had the following composition (in mol %).

$CF_3CH_2F$ 81.4350, $CF_3CH_2Cl$ 6.2400, $CHF_2CHF_2$ 0.1600, $CF_3CHF_2$ 0.5320, $CF_3CH_3$ 0.5360, $CF_3CHClF$ 0.5310, $CF_3CClF_2$ 0.0540, $CF_2=CHCl$ 0.4420, $CHCl=CHF$ 0.0020, HF 9.5060, and HCl 0.5620.

RAW MATERIAL EXAMPLE 2 (COMPARATIVE)

The crude purification product obtained by a reaction carried out in the same manner as in Raw Material Example 1 had the following composition (in mol %).

$CF_3CH_2F$ 71.4527, $CF_3CH_2Cl$ 12.2160, $CHF_2CHF_2$ 0.1820, $CF_3CHF_2$ 0.5620, $CF_3CH_3$ 0.6420, $CF_3CHClF$ 0.5880, $CF_3CClF_2$ 0.0570, $CF_2=CHCl$ 0.5820, $CHCl=CHF$ 0.0032, HF 8.3031, and HCl 5.4120.

EXAMPLE 1

A reactor, Inconel 600 type, measuring 1 inch in inner diameter and 1 m in length was filled with 80 ml of the catalyst of Catalyst Preparation Example 1. Prior to the reaction, the catalyst was fluorinated for activation with HF diluted with nitrogen and 100% HF.

The conditions for the treatment of the catalyst with the HF were as shown below.

Concentration of HF: 25 to 100%
Temperature of treatment: 250° to 350° C.
Time of treatment: about 10 hours In the presence of the activated catalyst prepared as described above, the raw material of Raw Material Example 1 was supplied to the reactor at a reaction temperature of 200° C. at a space velocity (SVo) of 1000 $hr^{-1}$. Acids were removed from the effluent gas, and then the resultant gas was analyzed by means of gas chromatography. Consequently, it was found to have the following composition (in mol %).

$CF_3CH_2F$ 90.5407, $CF_3CH_2Cl$ 7.4412, $CHF_2CHF_2$ 0.1779, $CF_3CHF_2$ 0.5916, $CF_3CH_3$ 0.5960, $CF_3CHClF$ 0.5904, $CF_3CClF_2$ 0.060, and $CH_2ClCHF_2$ 0.0021.

The $CF_3CH_2F$ was found to contain no detectable unsaturated impurity, indicating that the impurity was substantially removed by the treatment. No loss was found in the $CF_3CH_2F$, which was the desired product, and neither an increase nor a decrease was detected in other by-products.

Then, the reaction under the conditions described above was continued for 1000 hours. During the continued reaction, no reduction was detected in the removal efficiency of the unsaturated impurity and virtually no loss was found in the desired product, $CF_3CH_2F$.

The outlet gas was treated to remove the acid components, as described above, purified further by distillation, and analyzed. Consequently, the purified gas was found to have the following composition (in mol %).

$CF_3CH_2F$ 99.9976, $CHF_2CHF_2$ 0.0020, $CF_3CH_3$ 0.0001, $CF_3CHF_2$ 0.0002, and $CF_3CHClF$ 0.0001.

As a result, highly pure HFC-134a containing absolutely no unsaturated impurity was obtained.

EXAMPLE 2

A reaction was carried out by repeating the procedure of Example 1, except that the catalyst prepared as described in Preparation Example 2 was used instead. Thus, the outlet gas was treated to remove acid components and analyzed by means of gas chromatography.

The results of the analysis clearly show that no unsaturated impurity was detected in the produced $CF_3CH_2F$, a fact indicating substantially complete removal of the impurity, and that practically no loss was found in the desired product, $CF_3CH_2F$.

Comparative Experiment 1

A reaction was carried out by repeating the procedure of Example 1, except that the raw material of Raw Material Example 2 was used instead. Thus, the outlet gas was analyzed by means of gas chromatography. Consequently, it was found to have the following composition (in mol %).

$CF_3CH_2F$ 81.8828, $CF_3CH_2Cl$ 15.5915, $CHF_2CHF_2$ 0.2101, $CF_3CHF_2$ 0.6511, $CF_3CH_3$ 0.7446, $CF_3CHClF$ 0.6808, $CF_3CCl_2F$ 0.0658, $CF_2{=}CHCl$ 0.1484, $CHCl{=}CHF$ 0.0020, $CH_2ClCHF_2$ 0.0017, and $CClF_2CH_2Cl$ 0.0212.

Due to the high concentration of hydrogen chloride in $CF_3CH_2F$, the operation proved uneconomical because the removal efficiency of the unsaturated impurities fell to about 77.8% and the loss of $CF_3CH_2F$, the desired product, was about 1.1%.

Then, the reaction temperature was elevated to 280° C. and the outlet gas was treated to remove the acid components. The resultant gas was analyzed by means of gas chromatography.

The results of the test clearly indicate that the operation was not economical because the removal efficiency of unsaturated impurities rose to about 92% but failed to reach 100% as in Examples 1 and 2 and the loss of $CF_3CH_2F$, the desired product, increased to about 4.1%.

When the reaction was continued for 500 hours with the reaction temperature kept at 280° C., the removal efficiency of unsaturated impurities fell to about 80%. When the catalyst was observed, it was found to be deposited with carbon.

Comparative Example 2

The conventional process, i.e. the method of (1) mentioned above, was carried out. Activated alumina was kept immersed in an aqueous chromium chloride solution until it wholly absorbed the aqueous solution. It was then dried and calcined to obtain a fluorinating catalyst.

A second reactor was obtained by packing 80 ml of this catalyst in an Inconel 600 type reactor, measuring 1 inch in inner diameter and 1 m in length.

Separately, a reactor identical to the second reactor was filled with 80 ml of the catalyst produced by Catalyst Preparation Example 1 to produce a third reactor.

Prior to reaction, the catalysts in the second reactor and the third reactor were partially fluorinated with HF under the same conditions as described in Example 1, to activate the catalysts.

First, the second reactor was heated to 350° C. in a nitrogen atmosphere. Then, the supply of nitrogen was stopped. Hydrogen fluoride and HCFC-133a were supplied at respective flow rates of 1060 ml/min and 260 ml/min.

The outlet gas treated for removal of acid components was analyzed by means of gas chromatography. It was found to have the following composition (in mol %).

$CF_3CH_2F$ 3.88, $CF_3CH_2Cl$ 15.95, $CF_2{=}CHCl$ 0.024, other by-products 0.106, HCl 4.0, and HF 76.04.

Then, the third reactor was heated to 240° C. in a nitrogen atmosphere in the same manner as in the second reactor. The supply of nitrogen was stopped. The outlet gas from the second reactor (in the composition shown above) was introduced as it was to the third reactor. The outlet gas was treated to remove acid components. The gas was then analyzed by means of gas chromatography. It was found to have the following composition (in mol %).

$CF_3CH_2F$ 19.3248, $CF_3CH_2Cl$ 80.1352, $CF_2{=}CHCl$ 0.0072, and other by-products 0.5328.

The results show that the removal efficiency of unsaturated impurities from $CF_3CH_2F$ was about 94%, thereby indicating that the treatment was not very efficient.

Further, the operation was not economical because the operational efficiency was clearly inferior to that of Example 1 or 2 in view of the low purity of the desired $CF_3CH_2F$.

We claim:

1. A method for the purification of crude 1,1,1,2-tetrafluoroethane produced by reacting trichloroethylene with hydrogen fluoride, comprising bringing low hydrogen chloride content 1,1,1,2-tetrafluoroethane containing unsaturated impurities and having a concentration of hydrogen chloride of not higher than 2 mol %, and hydrogen fluoride in an amount at least equimolar to the unsaturated impurities, into contact with a fluorination catalyst in a vapor phase, so as to decrease the content of the unsaturated impurities, and comprising bringing the low hydrogen chloride content 1,1,1,2-tetrafluoroethane containing hydrogen fluoride into contact with the fluorination catalyst without further addition of hydrogen fluoride.

2. A method according to claim 1, wherein the low hydrogen chloride content 1,1,1,2-tetrafluoroethane contains 1,1,1,2-tetrafluoroethane in an amount of not less than 70 mol %.

3. A method according to claim 1, wherein the low hydrogen chloride content 1,1,1,2-tetrafluoroethane contains 1,1,1-trifluoro-2-chloroethane in an amount of not more than 10 mol %.

4. A method according to claim 1, wherein the catalyst is a compound of at least one metal selected from the group consisting of the metals of Groups 1B, 2A, 2B, 4B, 5A, 5B, 6A, 7A and 8 in the Long-Form Periodic Table of Elements.

5. A method according to claim 4, wherein the metal is selected from Cu, Mg, Zn, Pb, V, Bi, Cr, Mn, Fe, Co and Ni.

6. A method according to claim 1, wherein the contact of the low hydrogen chloride content 1,1,1,2-tetrafluoroethane with the catalyst is carried out at a temperature of 130° to 280° C.

* * * * *